(12) United States Patent
Kawai (10) Patent No.: US 8,517,925 B2
(45) Date of Patent: Aug. 27, 2013

(54) MEDICAL CONTROL SYSTEM

(75) Inventor: Toshimasa Kawai, Yokohama (JP)

(73) Assignee: Olympus Medical Systems Corp. (JP)

( * ) Notice: Subject to any disclaimer, the term of this patent is extended or adjusted under 35 U.S.C. 154(b) by 78 days.

(21) Appl. No.: 12/962,708

(22) Filed: Dec. 8, 2010

(65) Prior Publication Data
US 2011/0137122 A1 Jun. 9, 2011

Related U.S. Application Data

(63) Continuation of application No. PCT/JP2010/059955, filed on Jun. 11, 2010.

(30) Foreign Application Priority Data

Jun. 11, 2009 (JP) ................. 2009-140167

(51) Int. Cl.
*A61B 1/00* (2006.01)
(52) U.S. Cl.
USPC ............ 600/146; 600/145; 600/149; 600/152
(58) Field of Classification Search
USPC .................. 600/145, 146, 149, 152
See application file for complete search history.

(56) References Cited

U.S. PATENT DOCUMENTS 5,658,238 A * 8/1997 Suzuki et al. ................. 600/150
2004/0138530 A1* 7/2004 Kawai et al. .................. 600/152

FOREIGN PATENT DOCUMENTS

| JP | 3-17703 | 1/1991 |
|----|---------|--------|
| JP | 8-293074 | 11/1996 |
| JP | 2004-240516 | 8/2004 |
| JP | 2005-137701 | 6/2005 |
| JP | 2007-185355 | 7/2007 |

OTHER PUBLICATIONS

English Translation of International Search Report & Written Opinion mailed Jul. 20, 2010 in corresponding PCT International Application No. PCT/JP2010/059955.
International Search Report and Written Opinion mailed Jul. 20, 2010 in corresponding PCT International Application No. PCT/JP2010/059955.

* cited by examiner

*Primary Examiner* — Philip R Smith
*Assistant Examiner* — Rynae Boler
(74) *Attorney, Agent, or Firm* — Ostrolenk Faber LLP (57) ABSTRACT

In a medical control system, when motors are in a stopped state according to the determination based on an amount of change in an instruction value, the disturbance characteristics is set at high sensitivity in order to keep the detection capability of a disturbance observer section in an enhanced state during a period to the drive start time of the motors, and when the motors are brought into an operating state, a gain of a controller is returned to a normal setting value to maintain the excellent follow-up characteristics.

2 Claims, 7 Drawing Sheets

MEDICAL CONTROL SYSTEM

CROSS-REFERENCE TO RELATED APPLICATIONS

This is a Continuation Application of PCT Application No. PCT/JP2010/059955, filed Jun. 11, 2010, which was published under PCT Article 21(2) in Japanese.

This application is based upon and claims the benefit of priority from prior Japanese Patent Application No. 2009-140167, filed Jun. 11, 2009, the entire contents of which are incorporated herein by reference.

BACKGROUND OF THE INVENTION

1. Field of the Invention

The present invention relates to a medical control system used as a treatment tool inserted into a body cavity, and configured to acquire image information on an affected part to be medically treated or provide medical treatment.

2. Description of the Related Art

In general, an endoscopic apparatus inserted into a body cavity, and configured to be used to observe an affected part or the like is known. An insertion section of the endoscopic apparatus to be inserted into the body cavity is configured in such manner that a distal end part thereof can be freely curved in order that the insertion section may be moved back-and-forth along bends inside the body cavity, and those points and areas observation of which is desired may be imaged.

The curvature mechanism has a configuration in which the distal end part is divided into a plurality of short rods, and the rods are coupled to each other through joints. Each of these joints is connected to a wire to be thereby connected to an angle knob provided on the proximal end side. By operating the angle knob, the degree of traction of the wire is adjusted, whereby it is possible to freely curve the curvature mechanism.

In this curvature mechanism, the operator (observer) curves the insertion section by his or her own manual operation, and hence a heavy burden of the operation is imposed on the operator. In order to reduce such a burden, an electric-powered type mechanism using a motor is considered. More specifically, an electric drive source such as a motor is connected to each wire, the wires are pulled by the designation operation of switches provided at the operation section, thereby bending the joints. A technique of reducing the burden to be imposed on the operator by carrying out an operation aid in the manner described above is proposed.

The operation of delicately bending the insertion section involves electric drive means based on a switch operation, and hence the feeling of the operator differs from that of the manual operation, and the adjustment of the operation becomes difficult. For example, in the technique described in Pat. Document 1, a sensor configured to detect an amount of change (degree of bend) in the insertion section is provided to passively control the curvature drive section according to the detected amount of change. As the sensor, for example, a potentiometer and encoder are used, and a control amount of the curving operation of the curvature drive section is determined according to the detected amount of change and designation input based on the switch (angle knob).

BRIEF SUMMARY OF THE INVENTION

According to an embodiment of the present invention, there is provided a medical control system comprising: an insertion section which includes a curvature section provided with a plurality of joints to be traction-driven by means of wires, and is inserted into a body cavity; a drive section provided with a rotating shaft configured to rotate in accordance with a drive instruction signal; a reduce speed mechanism which is coupled to the rotating shaft, and is configured by engaging a plurality of gears with each other in order to change a rotational speed with respect to the rotational speed of the rotating shaft; a coupling section configured to couple the wires and the reduce speed mechanism to each other in order to operate the curvature section; a detection section configured to detect a rotation angle of the rotating shaft rotationally driven in accordance with the drive instruction signal; a determination section configured to determine a drive state of the drive section according to a change in the rotation angle detected by the detection section; a gain storage section in which a plurality of gains of a controller configured to generate the drive instruction signal for the drive section in a predetermined drive state are stored in accordance with a plurality of drive states; a gain adjustment section configured to acquire a controller gain corresponding to the drive state determined by the determination section from the gain storage section; and a control section configured to control the drive section by the drive instruction signal determined by the controller gain acquired by the gain adjustment section.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, embodiments of the present invention will be described below in detail with reference to the drawings.

Figure 1:
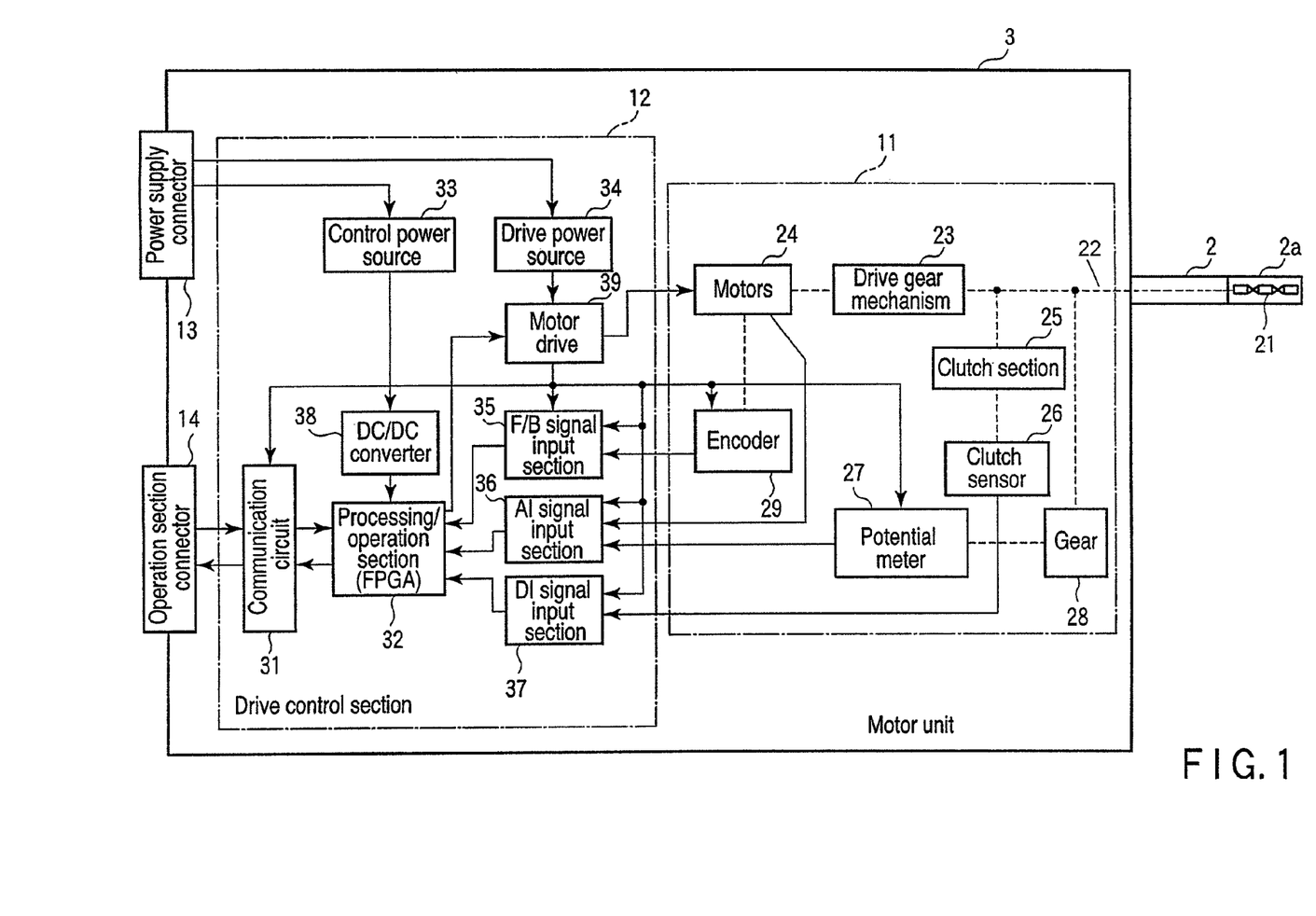
FIG. 1 is a view showing the internal configuration of a motor unit in a medical control system according to a first embodiment of the present invention.

FIG. 1 is a view showing the internal configuration of a motor unit in a medical control system according to a first embodiment of the present invention.

Figure 2:
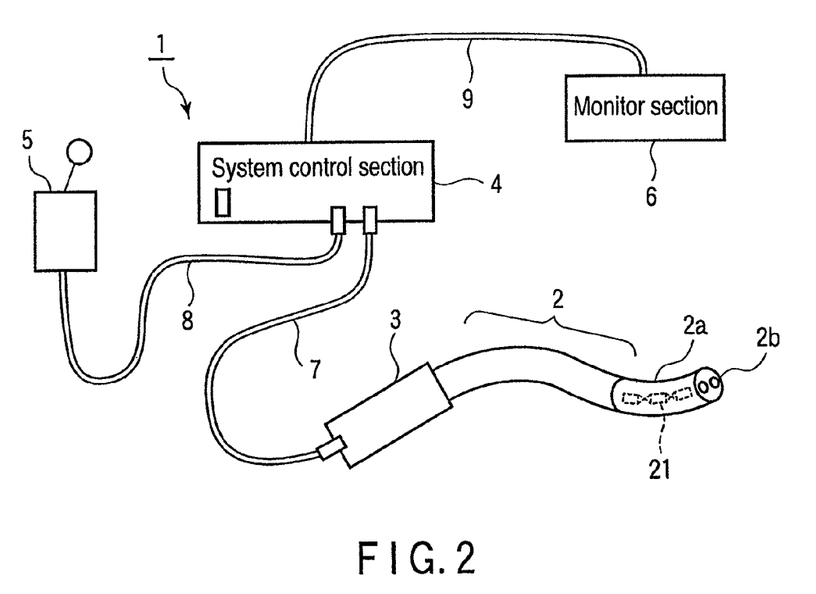
FIG. 2 is a view showing the schematic overall configuration of the medical control system according to the first embodiment.

FIG. 2 is a view showing the schematic overall configuration of the medical control system according to the first embodiment, regarding the following constituent parts of the first embodiment, only those necessary for explanation of the substance of the present invention are shown, it is assumed that constituent parts with which a general endoscopic apparatus is provided, such as a foot switch and the like are provided, and an illustration and description of these constituent parts are omitted.

A medical control system 1 of this embodiment is a master-slave medical control system configured to carry out a curving operation by means of a plurality of joints provided in an insertion section 2a of an endoscope main body 2 by traction of wires. This medical control system 1 is included a endoscope main body 2 an insertion section [insertion section] 2a of which is curved, motor unit [drive section] 3 provided at a distal end of the insertion section 2, system control section 4 configured to control the overall system, operation section 5 configured to give an instruction to curve the insertion section 2a to the system control section 4, and monitor section 6 configured to display a taken image.

The system control section 4 sends out, as control, a drive control signal to the motor unit 3 to carry out drive control, and subjects an image taken by an imaging section 2b provided at a distal end of the insertion section 2 to image processing.

The motor unit 3 is connected to the system control section 4 by means of a monitor-unit cable 7 through a connector. Likewise, the operation section 5, and monitor section 6 are connected to the system control section 4 by means of an operation-section cable 8, and monitor cable 9, respectively through connectors. Further, in a configuration in which the imaging section 2b is provided, although not shown, an image transmission line configured to send out image data taken by an imaging element to the system control section 4 is provided. Furthermore, although not shown, in the insertion section 2, a penetration hole extending from an insertion opening opened on the proximal end side to a distal end part, i.e., a so-called forceps channel used to pass a treatment tool configured to give medical treatment to an affected part therethrough, and light guide or lighting LED, and the like are provided.

In FIG. 1, a configuration example of the motor unit 3 is shown.

On the motor unit 3, a power supply connector 13, and operation section connector 14 to which a power supply line, and operation section line branched from the monitor-unit cable 7 extending from the aforementioned system control section 4 are connected, respectively are provided. It should be noted that in this embodiment, for the facility of understanding, although the connector is divided into two connectors for illustration, in the actual cables, there are cases where terminals in one connector are divided into those for power supply, and those for the operation section to thereby be used.

The motor unit 3 is roughly divided into a drive section 11 and drive control section 12.

The drive section 11 is provided with a plurality of motors 24 configured to pull wires 22 connected to a plurality of joints 21 arranged in a bending section 2a, drive gear mechanism 23 interposed between the motors 24 and wires, and configured to enhance the torque output from the motors 24, clutch section 25 configured to interconnect or disconnect transmission of drive force from the drive gear mechanism 23 to the wires 22, clutch sensor 26 having a switch structure, and configured to detect the on/off state of the clutch section 25, potential meter 27 configured to detect an absolute value of a current value of the motors 24, gear 28 provided to the wires 22 in order that the potential meter 27 may detect the absolute value, and encoder 29 provided to the motors 24 (or pulley not shown), and configured to acquire wire traction information.

Further, the drive control section 12 is an electronic circuit formed into, for example, an LSI chip. In this drive control section 12, a communication circuit 31 configured to carry out communication with the system control section 4, processing section (FPGA) 32 configured to receive a signal to be described later to carry out a servo operation or the like, and control power source 33 and drive power source 34 both of which constitute a power supply section are provided. Furthermore, in the drive control section 12, a feedback (F/B) signal input section 35 to which an output signal from the encoder 29 is input, analog input (AI) signal input section 36 to which a current signal applied to the motors 24 is input, and digital input (DI) signal input section 37 to which a signal indicating an absolute value from the clutch sensor 26 is input are provided.

Furthermore, the control power source 33 provides drive power obtained by stepping up or stepping down the original voltage to a DC voltage meeting the specification of the processing section 32 through a DC/DC converter 38. The drive power source 34 provides drive power to a motor drive 39 configured to drive the motors 24 according to a control signal from the processing section 32.

Figure 3:
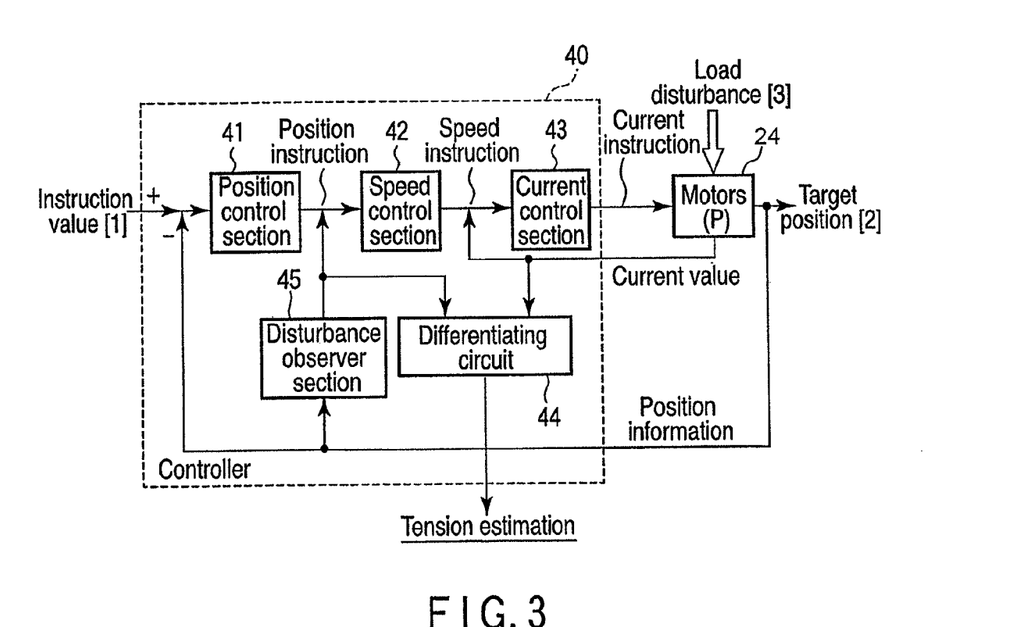
FIG. 3 shows a configuration example of a controller based on signal processing of a motor drive system provided in the motor unit 3 in the first embodiment.

FIG. 3 shows a configuration example of a controller based on signal processing of a motor drive system provided in the motor unit 3 in the first embodiment.

This controller 40 is constituted of a position control section 41, speed control section 42, current control section 43, differentiating circuit 44, and disturbance observer section 45.

In the configuration described above, the position control section 41 generates a position command based on a command value ([1] command) input from the operation section 5, and outputs the position command to the speed control section 42 as a position instruction. The speed control section 42 outputs a speed command generated according to the position command, and a current signal fed back and input to the motors 24 to the current control section 43 as a speed instruction. The current control section 43 generates a current command which becomes a traction drive amount for the wires according to the speed command, and outputs the current command to the motors 24 as a current instruction to thereby drive the motors. The motors 24 traction-drive the wires in such a manner that a target position [2] suggested by the current command is obtained.

Position information based on the target position is input from the motors 24 to the differentiating circuit 44 and position control section 41 to be fed back. The differentiating circuit 44 subjects position information items input thereto in time sequence to differential processing, and outputs the differential signal (motor positioning) to the speed control section 42 and disturbance observer section 45. Further, the disturbance observer section 45 receives the current signal input to the motors 24, and differential signal output from the differentiating circuit 44, and outputs a tension estimate value to be described later.

Further, when the motors 24 are driven, load disturbance [3] is applied to each of motor shafts of the motors 24 by the mechanical configuration. The load disturbance is equivalent to the reaction force of the wire traction, and hence can be detected as a load applied to the wires. Accordingly, without providing a sensor such as a tension sensor or the like, it is possible to estimate the load (tension amount) applied to the wires from the disturbance amount of the disturbance load.

The disturbance observer itself is already known to the public, and is used for various control purposes. The disturbance observer section 45 of this embodiment exists as an application program in the operation processing section such as a CPU or the like provided in the system control section 4.

Figure 4:
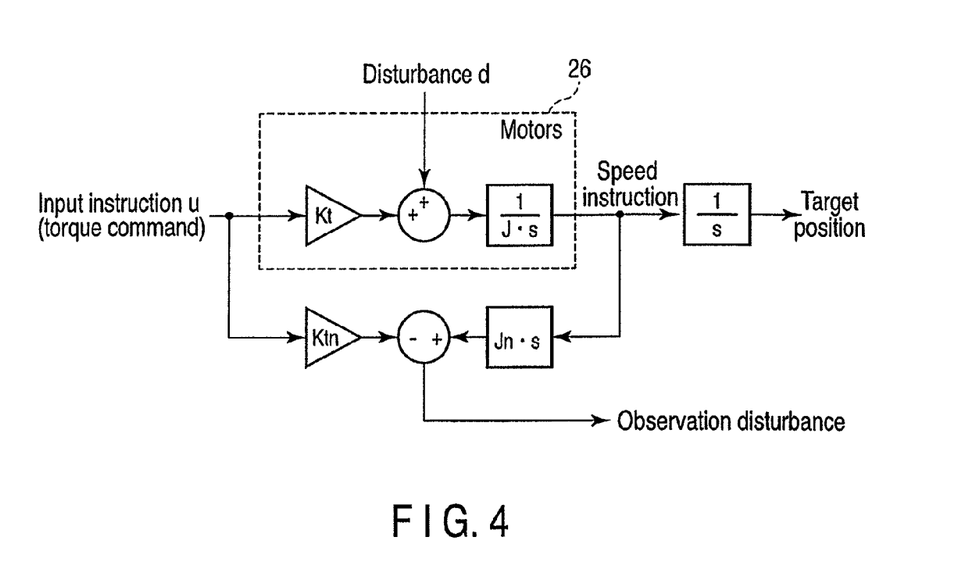
FIG. 4 is a block diagram of a motor model applied to the first embodiment.

FIG. 4 is a block diagram of a motor model applied to this embodiment.

An input instruction (wire traction drive amount: torque command) applied to the motors from the motor drive is a current instruction. In accordance with the current instruction, rotation and positioning of the motors is carried out. Further, the disturbance d to be input, and shown in FIG. 4 is assumed to be the disturbance load applied to the motor shafts.

In the actual motor model of this embodiment, the input instruction u (torque command) fed back from the motor drive 39 to be input thereto is a current instruction. According to this current instruction, a motor torque constant Kt is output. Then, the motor torque constant Kt and disturbance load d are added together, and the sum is divided by the product of a motor moment of inertia j and Laplace operator s. A quotient obtained by the division becomes the speed instruction, i.e., the motor rotational speed information (speed information), is divided by the Laplace operator s again, and is output as the motor target position information.

The disturbance observer section is arranged in such a manner that the section is parallel with a physical model identical with the actual motor model. The observation disturbance is obtained by multiplying a motor torque constant Kt' (catalog value) based on the input instruction u from the motor drive 39, and motor rotational speed information by a product (jn·s) of the motor moment of inertia jn (catalog value) and Laplace operator s. That is, the disturbance observer section obtains the inverse dynamics, and estimates the disturbance (tension) applied to the motor shafts from the information of the inverse dynamics.

Figure 5:
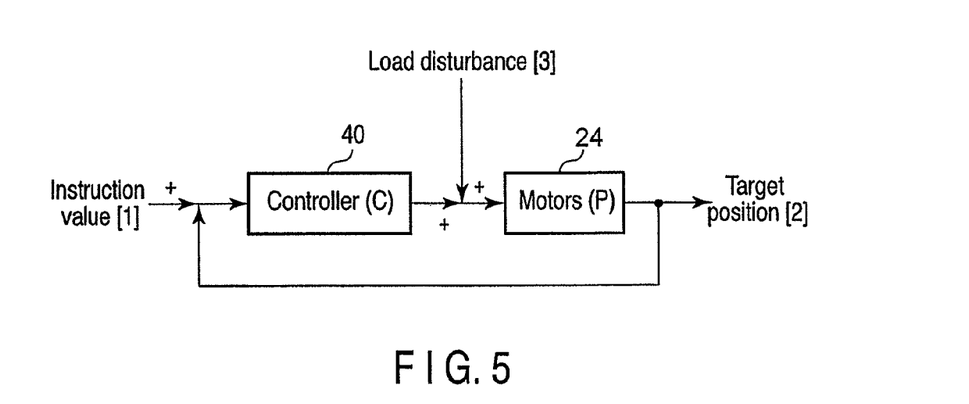
FIG. 5 is a view showing the configuration obtained by simplifying the signal processing of the motor drive system shown in FIG. 3.
Figure 6:
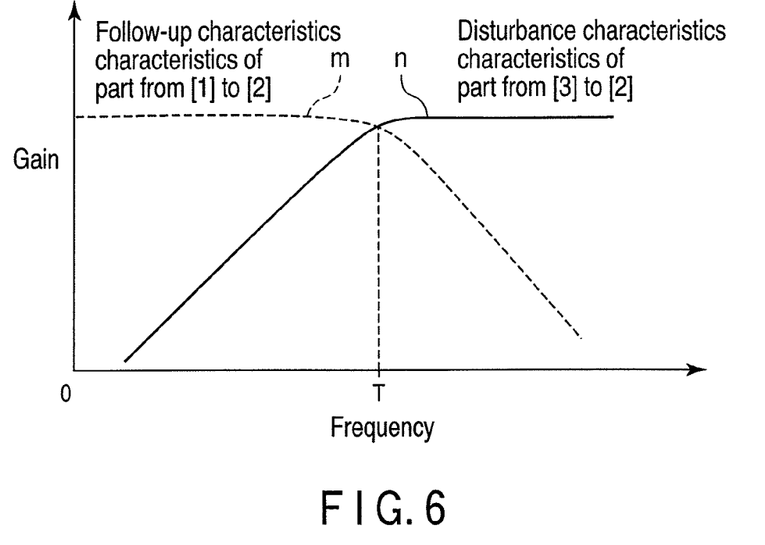
FIG. 6 is a view showing the follow-up characteristics and disturbance characteristics in the conventional relationship between gain and frequency.
Figure 7:
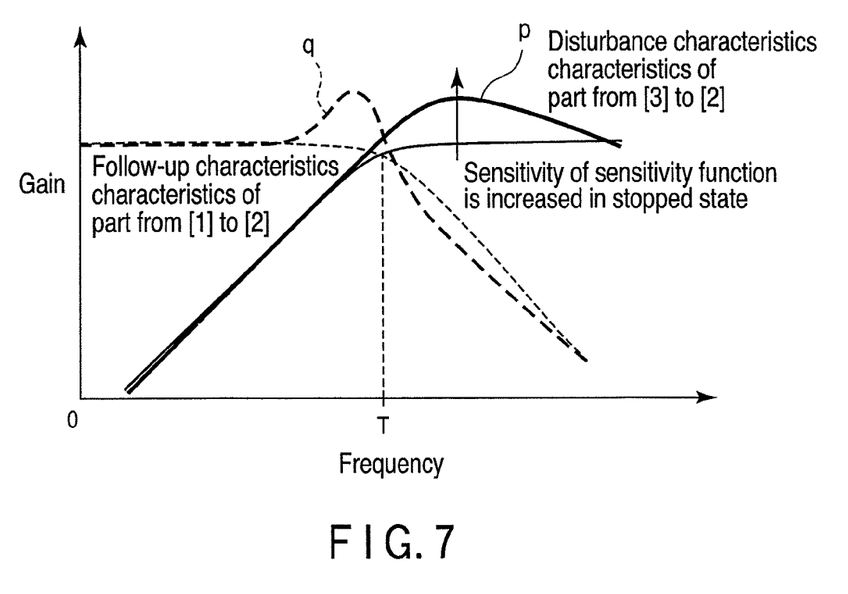
FIG. 7 is a view showing the follow-up characteristics and disturbance characteristics in the controller of this embodiment.

FIG. 5 shows the configuration obtained by simplifying the signal processing of the motor drive system shown in FIG. 3. FIG. 6 is a view showing the conventional relationship between gain and frequency, and shows the follow-up characteristics and disturbance characteristics. FIG. 7 is a view showing the relationship between gain and frequency in the controller 40 of this embodiment, and shows transfer of position, i.e., the follow-up characteristics and disturbance characteristics.

In FIG. 5, a current value suggesting a target position of the motors is fed back to the input side of the controller 40 through the feedback loop, and is input to the controller 40 together with the instruction value. The transfer from the instruction value [1] to the target position [2] of the motors is shown as the follow-up characteristics. The follow-up characteristics can be expressed by $C(s)P(s)/(1+C(s)P(s))$. However, $C(s)$ is the transfer characteristics of the controller, and $P(s)$ is the transfer characteristics of the motor model. Further, the transfer from the load disturbance [3] to the target position [2] of the motors is shown as the disturbance characteristics. The disturbance characteristics can be expressed by $P(s)/(1+C(s)P(s))$. However, $C(s)$ is the transfer characteristics of the controller, and $P(s)$ is the transfer characteristics of the motor model.

Regarding the follow-up characteristics and disturbance characteristics, setting cannot be changed individually, and both the characteristics have a mutually complementary relationship with respect to gain in frequency. For example, there is a relationship in which when the gain of the disturbance characteristics is increased, i.e., when the sensitivity is increased, the gain of the follow-up characteristics also becomes higher. When the gain of the follow-up characteristics is set too high, there occurs a problem or the like that when there is a change in the input signal, an overshoot or the like is caused to require a longer time to converge into one value. That is, the follow-up performance is deteriorated.

Theoretically, in the follow-up characteristics, the gain continues constant at a given value from a low frequency to a certain frequency T, and then attenuates to gradually and linearly descend from a point exceeding the frequency T as indicated by a broken line m. In the disturbance characteristics indicated by a solid line n, the gain linearly increases from a low frequency to a certain frequency T, and continues constant at a given value from a point exceeding the frequency T at which the disturbance characteristics intersect the follow-up characteristics.

As described previously, in order to enhance the detection performance by increasing the sensitivity for the disturbance, it is desired to set the gain of the disturbance characteristics high, and maintain the gain of the follow-up characteristics at a normal value.

Thus, in this embodiment, an amount of change in the instruction value is detected to determine whether the motors are in the operating state or in the stopped state. In this determination, when the motors are in the stopped state, the gain of the controller is increased from the normal setting value to a value desired as the gain of the disturbance characteristics to set the gain high (damping factor is made smaller) as indicated by a solid line p in FIG. 7. At this time, the follow-up characteristics of the case where the gain of the controller is set high become the characteristics in which the gain once shows one wave of an up/down change before the frequency T, passes the frequency T while descending down from the peak of the wave, and then linearly attenuates as indicated by a thick broken line q in FIG. 7. When the motors are driven, the motors do not smoothly rotate due to the up/down change of the gain, and rotate while being accompanied by vibration in some cases. It should be noted that the gain of the controller implies a parameter set in each of the position control section, speed control section, and current control section shown in FIG. 3. For example, in the case of the current control section, the gain is a parameter arbitrarily set to set an output value (current instruction) for the input value (speed instruction). These parameters are set in advance in a memory (not shown) provided in the drive control section 12 shown in FIG. 2, are read as the need arises, and are set in the respective configuration parts in a rewritable manner.

Thus, as described above, the controller 40 (see FIG. 3) constitutes a judgment section configured to judge whether the drive section is in an operating state or in a stopped state, based on a variation amount of the instruction value input from the operation section.

Thereafter, when it is determined that the motors are in the operating state according to the determination of the amount of change in the instruction value, setting for returning the gain of the controller to the normal setting value is carried out.

By such switching of the gain setting, it is possible to capture the load disturbance at high sensitivity in the stopped state, and it is possible to keep the detection capability of the disturbance observer section in an enhanced state during the period to the motor drive start time. Furthermore, concomitantly with the motor drive start, the gain of the disturbance characteristics which has been set high is returned to the original setting value, thereby preventing the follow-up characteristics from being adversely affected.

Accordingly, it is possible to obtain a disturbance amount of a high degree of accuracy by the disturbance observer section, and hence it is possible to estimate appropriate tension applied to the motors, and it becomes easy for the operator to carry out a delicate positioning operation by making the tension to be applied to the wires configured to drive the bending section appropriate. Furthermore, it is possible to omit a sensor exclusively used for detecting tension, thereby making it possible to contribute to reduction in size and weight of the motor unit.

Next, a second embodiment will be described below.

In the first embodiment described previously, although the gain of the disturbance characteristics is set high when the motors are in the stopped state, this embodiment is an example in which switching is carried out in such a manner that the frequency range becomes wider in order to enhance the sensitivity of the disturbance characteristics in the stopped state. It should be noted that the configuration of this embodiment is identical with the first embodiment described previously, constituent parts are denoted by using the identical reference symbols, and a description of them will be omitted.

Figure 8:
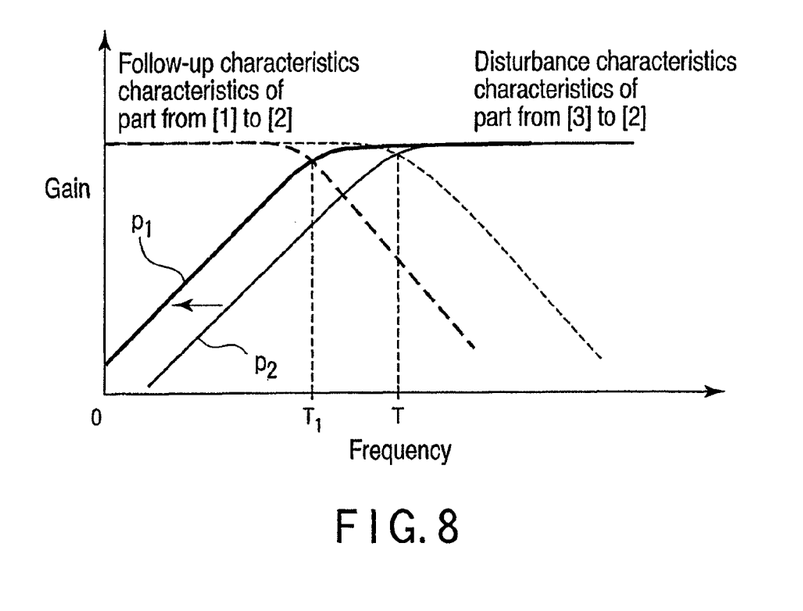
FIG. 8 is a view showing the follow-up characteristics and disturbance characteristics in a controller of a second embodiment.

FIG. 8 is a view showing a relationship between gain and frequency in a controller 40 of this embodiment, and shows a state where the follow-up characteristics and disturbance characteristics are switched.

In this embodiment too, the transfer from the instruction value [1] to the target position [2] of the motors is identical with the follow-up characteristics $C(s)P(s)/(1+C(s)P(s))$ described previously, and transfer from the load disturbance [3] to the target position [2] of the motors is the disturbance characteristics $P(s)/(1+C(s)P(s))$.

Thus, in this embodiment, an amount of change in the instruction value is detected to determine whether the motors are in the operating state or in the stopped state. When it is determined that the motors are in the stopped state, the setting value of the disturbance characteristics is switched from the ordinary setting value (thin solid line p2) of the frequency T at which the gain of the controller changes to a desired lower frequency T1 as indicated by a thick solid line in FIG. 8 to thereby set the setting value (cutoff frequency is lowered). At this time, in the follow-up characteristics too, the setting value is lowered from the frequency T indicated by a thin broken line in FIG. 8 to T1.

Thereafter, when it is determined that the motors are in the operating state according to the determination of the amount of change in the instruction value, the setting value is switched from the set frequency T1 to the frequency T to restore the characteristics to the normal state.

That is, by changing the frequency to a lower frequency in the inspection band when the motors are in the stopped state, it is possible to make the gain higher, capture the load disturbance at high sensitivity, and keep the detection capability of the disturbance observer section in an enhanced state during the period to the motor drive start time. Furthermore, concomitantly with the motor drive start, the frequency which has been set low is returned to the normal state.

From the above description, according to this embodiment, by setting the gain high when the motors are in the stopped state, it is possible to start the operation of the motors in a state where the sensitivity of the disturbance characteristics is set high. Further, the gain of the disturbance characteristics is returned to the original state by switching the frequency to the normal setting frequency concomitantly with the operation start, thereby preventing the follow-up characteristics from being adversely affected.

Accordingly, it is possible to obtain an advantage identical with the advantage of the first embodiment described previously. That is, it is possible to estimate appropriate tension applied to the motors, appropriately drive the bending section, and it becomes easy to carry out a delicate positioning operation. Furthermore, it is possible to omit a sensor exclusively used for detecting tension, thereby making it possible to contribute to reduction in size and weight of the motor unit.

Thus, the controller 40 (FIG. 3), as described above, also constitutes a controller setting section configured to set the controller, when it is judged by the judgment section that the drive section is in an operating state, to have preset first disturbance characteristics from a disturbance noted onto the rotating shaft from the curvature portion via the wire, the cross-section and the drive gear mechanism, or set the controller, when it is judged by the judgment section that the drive section is in the stopped state, to have preset second disturbance characteristics from a disturbance.

Next, a third embodiment will be described below.

In the first and second embodiments described previously, although switching of the gain has been carried out when the motors are in the stopped state or when the operational state is switched, this embodiment is configured in such a manner that when the motors are in the stopped state, in addition to rewriting of the gain, a compensation element (FB) is inserted into the feedback loop by switching.

Figure 9:
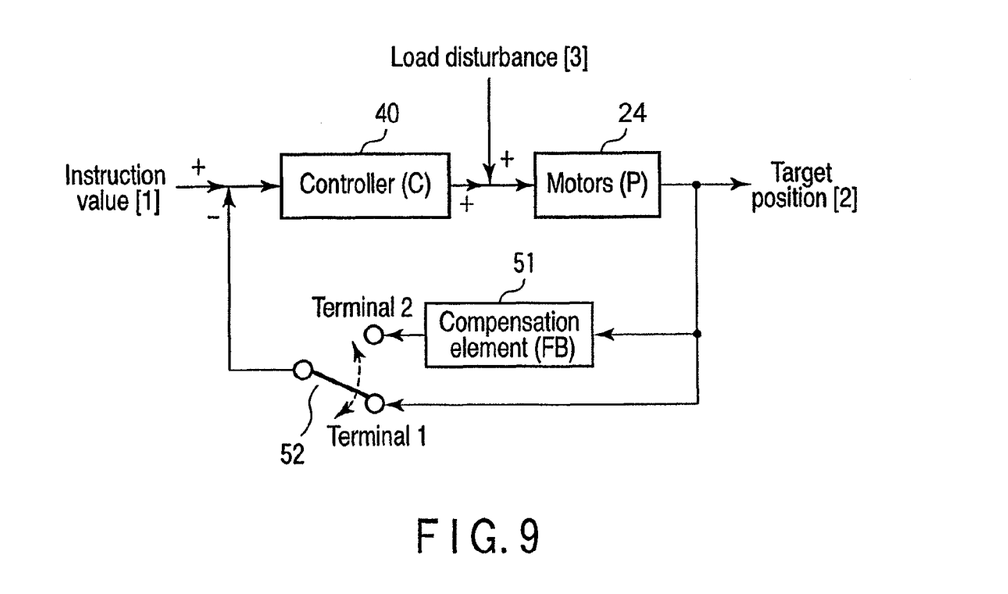
FIG. 9 is a view showing the configuration obtained by simplifying the signal processing of a motor drive system of a third embodiment.
Figure 10:
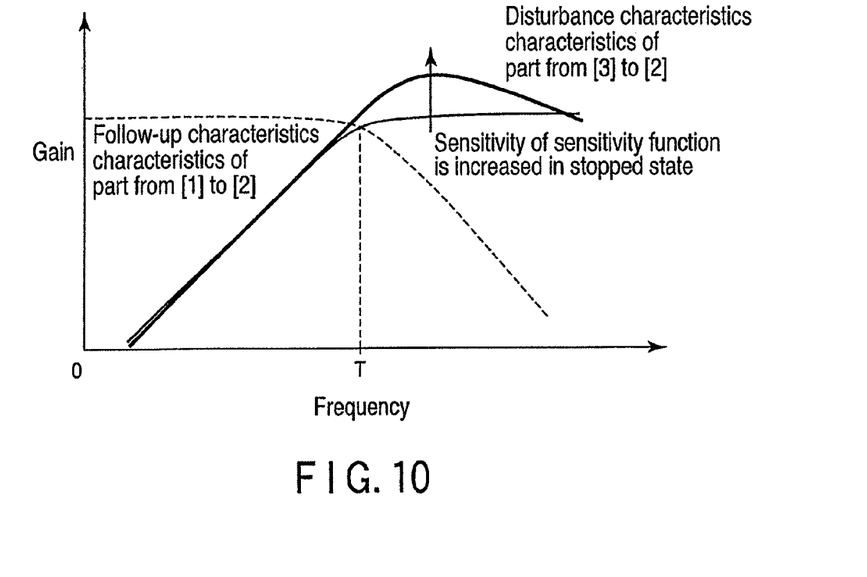
FIG. 10 is a view showing the follow-up characteristics and disturbance characteristics in a controller of the third embodiment.

FIG. 9 is a view showing the configuration obtained by simplifying the signal processing of a motor drive system. FIG. 10 is a view showing the follow-up characteristics and disturbance characteristics in a controller of this embodiment.

This embodiment is a configuration example in which in addition to the aforementioned controller (C) 40 and motors (P) 24, a compensation element (FB) 51 and changeover switch 52 are arranged in the feedback loop from the motors (P) 24 to the controller (C) 40. The compensation element (FB) 51 is a processing section provided in a program (or application software) and, more specifically, is constituted of a setting program configured to increase the sensitivity of the disturbance by setting the gain high in a certain frequency band, i.e., in a band from a frequency T to an upper limit frequency T2 in this embodiment. Further, the changeover switch 52 is also constituted of a program configured to carry out a switching operation in the similar manner.

In this embodiment, when the motors normally operate, the changeover switch 52 is connected to a terminal 1, and the connection configuration is identical with that at the time of the follow-up characteristics of the first embodiment described previously. On the other hand, when it is determined that the motors are in the stopped state, the changeover switch 52 is switched from the terminal 1 to a terminal 2 to insert the compensation element (FB) 51 into the feedback loop. By capturing the compensation element (FB) 51, setting is carried out in such a manner that the gain is set higher than at normal times to form a shape of an arching curve in the frequency range from the frequency T to the upper limit frequency T2 as shown in FIG. 10.

Further, when it is determined that the state of the motors has been switched from the stopped state to the operating state, the operation of the motors is started, and the changeover switch 52 is switched from the terminal 2 to the terminal 1 to return the configuration to the normal configuration in which the compensation element (FB) 51 is detached from the configuration.

As described above, according to the configuration of this embodiment, an advantage identical with the first embodiment can be obtained. Furthermore, according to this embodiment, the compensation element (FB) 51 is inserted into or removed from the feedback loop used to carry out feedback from the motors to the controller by means of a changeover switch 52. By virtue of the insertion/removal, switching can be unitarily carried out by the parameter (or coefficient) of the compensation element (FB) 51 without changing a plurality of gains in the controller, and hence setting of gain changing becomes easy. Further, the compensation element (FB) 51 is also constituted of a program or the like, and hence neither the substantial space in the system is used, nor the problem of size enlargement or the like is caused.

Next, a fourth embodiment will be described below.

Figure 11:
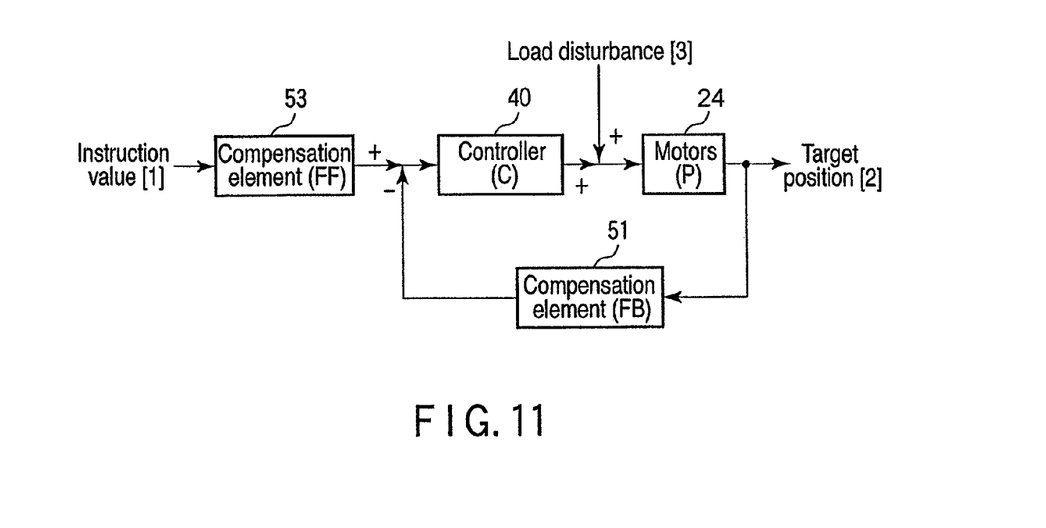
FIG. 11 is a view showing the configuration obtained by simplifying the signal processing of a motor drive system of a fourth embodiment.
Figure 12:
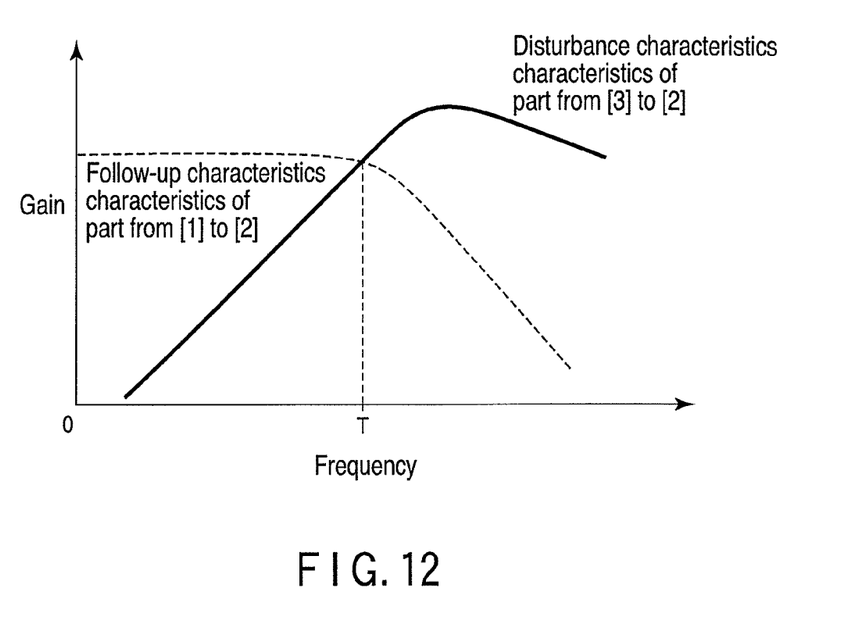
FIG. 12 is a view showing the follow-up characteristics and disturbance characteristics in a controller of the fourth embodiment.

FIG. 11 is a view showing the configuration obtained by simplifying the signal processing of a motor drive system of this embodiment. FIG. 12 is a view showing the follow-up characteristics and disturbance characteristics in a controller 40 of this embodiment. In the third embodiment described previously, although insertion/removal of the compensation element (FB) 51 into/from the feedback loop has been carried out by means of the changeover switch, this embodiment is a configuration example in which a compensation element (FF) is arranged in the preceding stage of a controller (C) 40, and compensation element (FB) is arranged in the feedback loop from motors (P) 24 to a controller (C) 40.

The compensation element (FF) and compensation element (FB) are processing sections provided in a program (or application software). The compensation element (FB) functions to carry out compensation of increasing the gain of the disturbance characteristics as shown in FIG. 10. The compensation element (FF) functions to carry out compensation of returning the compensation carried out by the compensation element (FB) to the gain of the disturbance characteristics at normal times.

In FIG. 11, the transfer from the instruction value [1] to the motor target position [2] is shown as the follow-up characteristics. The follow-up characteristics can be expressed by $C(s) \cdot P(s) \cdot FF(s)/(1+C(s) \cdot P(s) \cdot FB(s))$. However, $C(s)$ is the transfer characteristics of the controller, $P(s)$ is the transfer characteristics of the motor model, $FF(s)$ is the transfer characteristics of the compensation element (FF), and $FB(s)$ is the transfer characteristics of the compensation element (FB). Further, the transfer from the load disturbance [3] to the motor target position [2] is shown as the disturbance characteristics. The disturbance characteristics can be expressed by $P(s)/(1+C(s) \cdot P(s) \cdot FB(s))$. However, $P(S)$ is the transfer characteristics of the motor model, $FF(s)$ is the transfer characteristics of the compensation element (FF), and $FB(s)$ is the transfer characteristics of the compensation element (FB).

Regarding the follow-up characteristics shown in FIG. 12, by simultaneously inserting both the transfer characteristics of the compensation element (FF), and those of the compensation element (FB), both the compensation effects cancel each other at the point at which they are input to the controller 40, and the follow-up characteristics become the characteristics identical with the first embodiment. Further, regarding the disturbance characteristics, by employing the compensation element (FB), the detection sensitivity is increased in accordance with the frequency irrespectively of whether the motors are in the stopped state or in the operating state. In the disturbance characteristics, compensation is carried out to increase the gain of the controller in the frequency range higher than the frequency T as indicated by a thick solid line p1 in FIG. 12.

As described above, according to this embodiment, regarding the gain of the disturbance characteristics, i.e., the sensitivity, the detection sensitivity can be increased in accordance with the frequency irrespectively of whether the motors are in the stopped state or in the operating state, in the follow-up characteristics, compensation produced by the compensation element (FB), and the compensation of the compensation element (FF) cancel each other, i.e., the gain is returned to the gain at normal times, and hence neither determination of whether the motors are in the stopped state or in the operating state is necessary, nor a switching section such as a switch or the like in the feedback loop is necessary.

Accordingly, in this embodiment, a function and advantage identical with the first embodiment can be obtained. Furthermore, in this embodiment, the determination of whether the motors are in the stopped state or in the operating state becomes unnecessary, in the disturbance characteristics, with respect to a frequency range in which the sensitivity is desired to be increased, the gain is increased by subjecting the fed back signal to arbitrary compensation, and in the follow-up characteristics, the compensation associated with the disturbance characteristics is canceled, whereby the follow-up performance can be prevented from being deteriorated.

It should be noted that the invention based on the embodiments described previously can also be carried out by combining the embodiments with each other, even when a constituent element other than the substance of each embodiment is deleted, the invention can be realized, and it is possible to obtain the function and advantage of the present invention.

According to the embodiments described above, the following inventions are included in the embodiments.

(1) A medical control system characterized by comprising:
insertion means which is inserted into a body cavity, and in which wires are provided;
drive means for driving the wires to curve the insertion means;
instruction input means for inputting a curvature instruction amount to the wires;
control means for carrying out drive control in the insertion means according to the curvature instruction amount from the instruction input means;
detection means for detecting a change in the curvature instruction amount input to the instruction input means; and
disturbance estimation means for adjusting, when it is determined that the state is a stopped state from a change in a curvature drive amount according to a detection result of the detection means, the acquisition sensitivity of disturbance information generated by the drive means to estimate a disturbance amount, wherein
drive control of the insertion means is carried out according to the disturbance amount estimated by the disturbance estimation means.

(2) The medical control system according to (1), characterized in that the disturbance estimation means increases gain with respect to frequency in the control means.

(3) The medical control system according to (1), characterized in that the disturbance estimation means decreases gain with respect frequency in the control means.

(4) The medical control system according to (1), characterized in that the disturbance estimation means carries out compensation of increasing the sensitivity of the disturbance information from the frequency-gain follow-up characteristics.

(5) The medical control system according to (1), characterized in that the disturbance estimation means provides compensation to the input drive amount regardless of the detection result of the detection means, and carries out compensation of increasing the sensitivity of the disturbance information.

According to the present invention, it is possible to provide a medical control system in which disturbance information is accurately reflected in the control to be carried out according to the curvature instruction amount used for controlling the curving operation, and amount of change in an insertion section with respect to an endoscope including the insertion section to be bent by the electric power operation.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical control system comprising:
   an insertion section which includes a curvature section provided with a plurality of joints to be traction-driven by means of wires, and is inserted into a body cavity;
   a drive section provided with a rotating shaft configured to rotate in accordance with a drive instruction signal;
   a drive gear mechanism which is coupled to the rotating shaft, and is configured to transmit a drive torque larger than a torque generated by the drive section to the wires;
   a clutch section configured to couple the wires and the drive gear mechanism to each other in order to operate the curvature section;
   a detection section configured to detect a rotation angle of the rotating shaft;
   an operation section configured to input an instruction value to drive the drive section;
   a judgment section configured to judge whether the drive section is in an operating state or in a stopped state, based on a variation amount of the instruction value input from the operation section;
   a controller configured to generate the electrical current instruction signal to be output to the drive section to tract the wires to a target position, based on the instruction value;
   a controller setting section configured to set the controller, when it is judged by the judgment section that the drive section is in the operating state, to have preset first disturbance characteristics for a disturbance loaded onto the rotating shaft from the curvature portion via the wire, the clutch section and the drive gear mechanism, or to set the controller, when it is judged by the judgment section that the drive section is in the stopped state, to have preset second disturbance characteristics for the disturbance;
   a control section configured to output to the drive section the electrical current instruction signal generated based on the controller set by the controller setting section; and
   wherein the second disturbance characteristics make a sensitivity higher than the first disturbance characteristics.

2. The medical control system according to claim 1, wherein
   the second disturbance characteristics include a characteristic which accompanies vibration of the rotating shaft against the disturbance.

* * * * *